United States Patent
Bernhardsson et al.

(10) Patent No.: US 7,250,302 B2
(45) Date of Patent: Jul. 31, 2007

(54) MEASURING METHOD AND SYSTEM AND USE OF THE METHOD AND SYSTEM

(75) Inventors: Sven Bernhardsson, Rattvik (SE); Johan Liljha, Rattvik (SE); Leif Pellas, Rattvik (SE)

(73) Assignee: Siljan Allards AB, Rattvik (SE)

(*) Notice: Subject to any disclaimer, the term of this patent is extended or adjusted under 35 U.S.C. 154(b) by 608 days.

(21) Appl. No.: 10/311,966

(22) PCT Filed: Jun. 25, 2001

(86) PCT No.: PCT/SE01/01455

§ 371 (c)(1),
(2), (4) Date: Mar. 21, 2003

(87) PCT Pub. No.: WO02/01196

PCT Pub. Date: Jan. 3, 2002

(65) Prior Publication Data
US 2003/0184754 A1    Oct. 2, 2003

(30) Foreign Application Priority Data
Jun. 26, 2000  (SE) ..................................... 0002403

(51) Int. Cl.
*G01N 30/00*  (2006.01)

(52) U.S. Cl. .................. 436/49; 436/180; 422/68.1; 422/81; 422/82.05

(58) Field of Classification Search .................. 436/49, 436/8, 43; 422/55, 68.1, 81, 82.05
See application file for complete search history.

(56) References Cited

U.S. PATENT DOCUMENTS 5,185,531 A * 2/1993 Wynn .......................... 250/431
2004/0060576 A1* 4/2004 Cronin et al. ................... 134/7

FOREIGN PATENT DOCUMENTS

DE          3538313      * 10/1995

* cited by examiner

*Primary Examiner*—Jill Warden
*Assistant Examiner*—Sam P. Siefke
(74) *Attorney, Agent, or Firm*—Young & Thompson

(57) ABSTRACT

A method for optical measuring of the solid substance content in a fluid uses periodical flushing of an optical sensor (1) with a combination of pressurized air and water in the form of a jet. The jet exerts a very powerful cleaning effect without causing scratches on measuring surfaces of glass or similar materials. The invention also relates to a system for performing such flushing in connection with measuring.

19 Claims, 1 Drawing Sheet

MEASURING METHOD AND SYSTEM AND USE OF THE METHOD AND SYSTEM

TECHNICAL FIELD

The present invention relates to optical measuring of solid substance in fluids and relates more specifically to a method and a system for performing such a measurement in a manner that is reproducible and constant over time.

BACKGROUND

For many years, attempts have been made to develop optical methods for measuring particles, i.e. sludge, in fluids. Within this context, fouling or contamination of a sampler or tester is a serious problem that risks making the measurement result entirely or partly useless after a certain operating time. The development of optical testers has therefore included different alternative methods of cleaning the tester, such as the use of wind-screen wipers on the glass surface transmitting the optical radiation, water flushing to keep the surface clean and the use of a brush for mechanical or manual cleaning. No existing testers have worked satisfactorily, but there has been clogging and in the case of mechanical cleaning scratches have often developed on the measuring surface, which has lead to unreliable measurement results.

The testers have throughout been positioned down in a tank containing sludge or in a line containing sludge, which has made the tester difficult to reach for inspection and attendance, for instance by mechanical cleaning.

As a consequence, this measuring technique has not been working properly and it has not been possible to measure sludge content in a reliable manner.

SUMMARY OF THE INVENTION

The basic object of the present invention is to eliminate the described shortcomings that are related to the known technique within this field, so that the sludge content may be measured during long periods of time and with stable results.

According to the invention, the above stated object is achieved by providing a method of optical measuring, which uses a combination of pressurized air and water as a jet-beam by flushing. In this field of application, such a combination has provided a very powerful cleaning effect without causing scratches on measuring surfaces of glass or similar materials.

According to one embodiment of the invention, the method is used in combination with an intelligent computer based control unit by means of which the frequency of flushing, sampling and measuring is selected and controlled, the flushing being performed in a specific sequence providing maximum cleaning effect before the measurement.

According to another embodiment the sampler is made easily accessible for inspection and manual attendance by positioning the sampler separated from the actual sludge tank or sludge line. This considerably facilitates operation and handling.

According to still another embodiment the sampler is positioned above the sludge-containing line or container and is connected thereto through a hose or pipe line, the fluid/sludge mixture being transported up to the sensor/sampler by means of vacuum or pressure.

According to further embodiments a cleaning agent may be added by difficult combinations of fluid and sludge; a fouling alarm may be used so that a supplementary manual cleaning with a brush or a mechanized cleaning with a brush is performed only when needed. This minimizes the impact on the measuring surface. A cleaning agent may also be added when the fouling alarm is activated.

Further embodiments of this first aspect of the invention are specified in the corresponding dependent claims.

Another object of the invention is to provide an appropriate system for performing reliable optical measuring according to the invention.

According to another aspect of the invention is suggested a system for optical measuring of the sludge content of a fluid, which comprises an optical sensor and a combined supply of pressurized air and water forming a jet stream for cleaning the sensor.

Embodiments of this aspect of the invention are evident from the corresponding dependent claims.

According to still another aspect of the invention is suggested the use of a method as well as a system according to the invention for providing reliable measurement results for thickening and dewatering processes.

These and other objects of the invention are achieved by the invention as defined in the appended claims.

Briefly, the present invention offers the following advantages:

Through effective cleaning, reliable measurement results can be obtained even by difficult conditions;
Enables effective control of the sequences of flushing, sampling and measuring;
Improved accessibility and simplified inspection and as a consequence thereof a more effective and inexpensive operation, by normal conditions as well as when specific actions are required;
A minimum risk of scratches or other damages occurring at the measuring equipment.

Further objects, characteristics and advantages of the invention, as well as further embodiments thereof, are evident from the following description of exemplary embodiments.

DESCRIPTION OF THE DRAWING

The invention will now be described in detail with reference to the appended drawing FIG. 1, which is a simplified diagram disclosing exemplary embodiments of a measuring system according to the invention.

DESCRIPTION OF EXEMPLARY EMBODIMENTS

Figure 1:
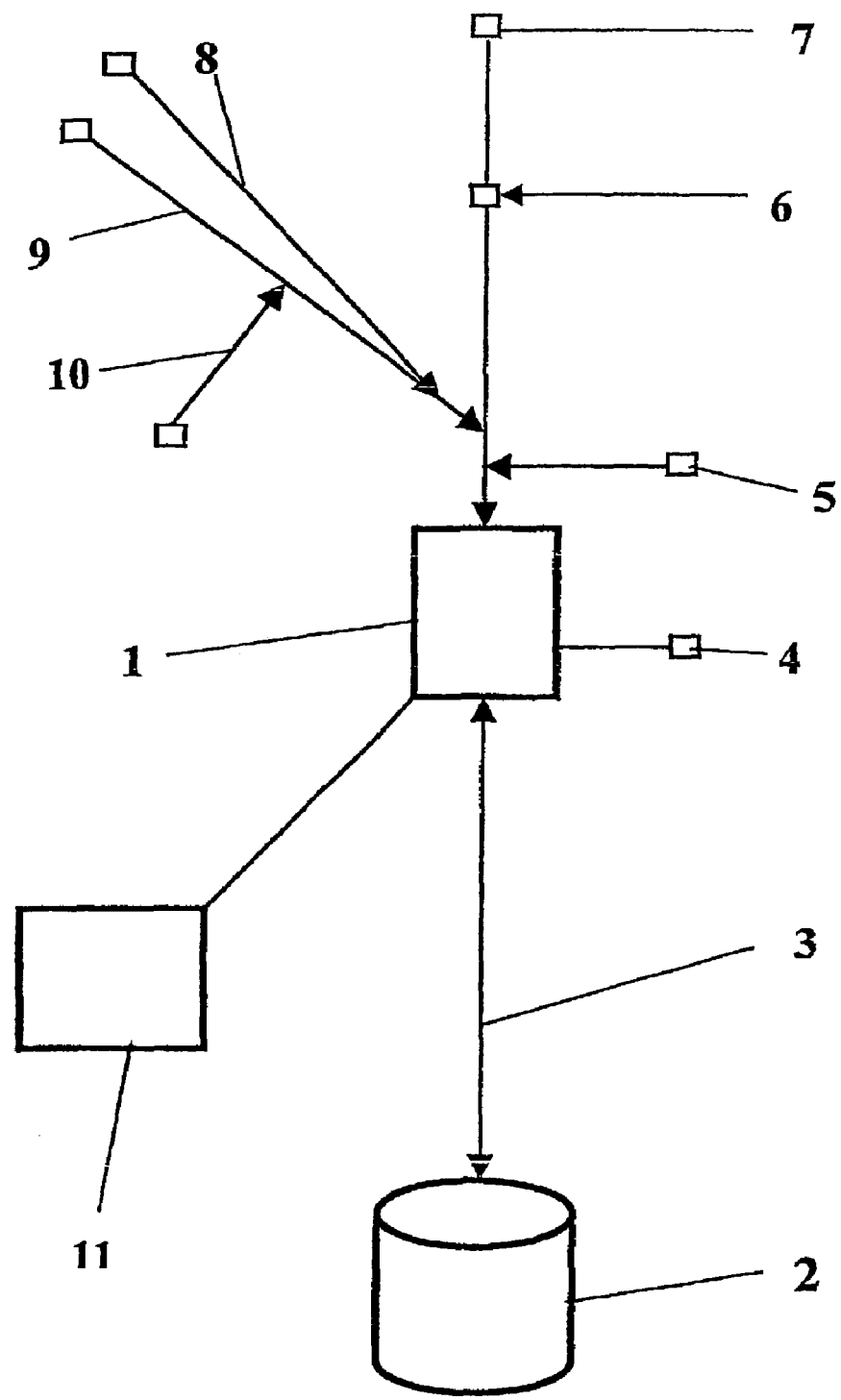

With reference to the drawing figure, the basic principles of the invention will now be described by means of a number of presently preferred embodiments of the invention and at the same time differences compared to conventional technique will be explained.

EXAMPLE 1

As was stated initially, the basic object of the invention is to accomplish a sludge content measurement that is stable over time and therefore reliable. This is achieved by means of a method for preventing permanent fouling of an optical measuring device 1, while simultaneously eliminating the risk of damages to the measuring device caused by the cleaning.

This first embodiment relates to a sludge content measurement where a sensor/sampler 1 is positioned above a sludge container or sludge line 2. Here cleaning is performed with a jet of pressurized air and water and the frequency of flushing, sampling and measuring is selected in and controlled by a control box 11. The sensor/sampler 1 is preferably arranged in working height, easy to reach for attendance, visual control and possible sensor unit replacement.

According to this embodiment of the present invention, which is shown in the drawing, this is achieved by connecting the sensor 1 to the sludge-containing line or container 2 through a hose or pipe line 3. A vacuum pump or a pressure generating pump (not shown) feeds the sludge to the sensor in sequences controlled by the computerized control box 11 via a system of valves (not shown).

The measurement sequence begins with flushing of the sensor with a jet (stream) of pressurized air, supplied through a line 8, and water, supplied through a line 9. The lines 8, 9 are joined upstream of the optical sensor and the jet formed of pressurized air and water is directed at an angle to a pipe where the sensor is positioned, i.e. towards a measuring surface of the sensor that is not specifically shown. The angle is between 0 and 90 degrees, preferably between 10 and 80 degrees, and the inlet of the jet stream is positioned as close as possible to the sensor.

Then, sludge is pumped up to the sensor 1, whereupon a level monitor 5, being capable of visual fouling evaluation, closes the pump as the sludge has reached the desired level. Then, the sludge content is measured with the optical sensor 1, for a predetermined period of time, whereafter flushing with water and pressurized air is performed. This is then repeated at predetermined time intervals during the time of measuring, which lasts for several months.

EXAMPLE 2

This example concerns a sludge content measurement where the sampler/sensor 1 is positioned above the sludge container/line 2. Here, cleaning is performed by means of a jet stream of pressurized air and water and the frequency of flushing, sampling and measuring is selected in and controlled by a control box 11. The optical sensor 1 has a detecting or sensing function of a fouling alarm 4 that indicates when manual mechanical cleaning may be required.

Although flushing with the combination of pressurized air and water has shown to be very efficient for cleaning the measuring surface, there may be applications containing sludge that is very adhesive or sticky to the measuring surface and that consequently results in fouling after a certain period of time. When this is the case, the fouling alarm 4 reacts, which is based on optical technique and consists of a combination of signals from the level monitor and the sensor. An alarm signal is then provided, whereupon the operator may clean the measuring surface manually using a brush at a connection 7. Since this cleaning is performed with long time intervals, the measuring surface is not affected by scratch formation to any appreciable extent.

EXAMPLE 3

This example concerns a sludge content measurement, where the sampler 1 is positioned above the sludge container/line 2. Here, cleaning is performed by means of a jet stream of pressurized air and water and the frequency of flushing, sampling and measuring is selected in and controlled by a control box 11. A fouling alarm 4 initiates the addition of a cleaning agent 10 by emitting the corresponding alarm signal.

The measurement is performed according to example 1 or 2, but the sludge particles are very adhesive to the measuring surface. The fouling alarm 4 initiates an addition of a cleaning agent through a line 10 connected to the water supply line 9. In combination with flushing with pressurized air and water, the addition of the cleaning agent minimizes the risk of permanent fouling. Thereby the need for mechanical cleaning is eliminated.

EXAMPLE 4

This example concerns a sludge content measurement, where the sampler 1 is positioned above the sludge container/line 2. Here, cleaning is performed by means of a jet stream of pressurized air and water and the frequency of flushing, sampling and measuring is selected in and controlled by a control box 11. A fouling alarm 4 starts a mechanical cleaning of the measuring surface, with or without the addition of the cleaning agent 10, by means of a power-driven brush 6 or a brush driven by pressurized air/water, said brush being activated when the fouling alarm 4 is activated.

Here, the measurement is performed according to example 1, 2 or 3, but the sludge particles are very adhesive to the measuring surface. The fouling alarm 4 starts a mechanized cleaning of the measuring surface of the sensor for a pre-selected period of time. In combination with the flushing with pressurized air and water and a possible cleaning agent addition, this increases the cleaning effect such that the risk of permanent fouling is minimized. In this way, a combination of several cleaning methods is obtained, while mechanical damaging of the measuring surface is minimnized.

Although the invention may be used generally for measuring fluids having a sludge content, it is presently considered that its most important application concerns thickening and dewatering equipment where measurement results via the control unit is used to control the thickening and dewatering processes.

The man skilled in the art recognizes that various modifications and changes can be made to the present invention without departing from the scope thereof, as defined by the appended claims.

The invention claimed is:

1. A method for ensuring reliable measurement values when measuring the content of solid substance in a fluid with an optical sensor/sampler, by periodical cleaning of the sensor/sampler through flushing thereof with a combination of water and pressurized air supplied through water and pressurized air lines, respectively, and in the form of a jet stream, the method comprising the steps of:
   a) arranging the sensor/sampler above a sludge container or sludge line and connecting the sensor/sampler to said container or line through a hose or pipe line so that the sensor is permanently provided separate from the body of the solid substance content of which is to be measured;
   b) initiating a measurement sequence by flushing the sensor/sampler with said jet stream of pressurized air and water;
   c) feeding sludge from said sludge container or sludge line to the sensor/sampler with one of a vacuum pump and a pressure generating pump;
   d) measuring the content of solid substance in the fluid with the optical sensor/sampler for a predetermined period of time so that the sensor is not submerged in the fluid but is only exposed to said fluid during the actual measuring period; and
   e) repeated flushing of the sensor/sampler with water and pressurized air.

2. A method according to claim 1, wherein the flushing with the jet stream is performed in a determined sequence and in the frequency of flushing, as well as sampling and measuring, is selected and controlled by a computer based control box.

3. A method according to claim 1, wherein said measuring sequence is then repeated at predetermined intervals during a time of measurement.

4. A method according to claim 1, wherein said jet stream comprising of a combination of water and pressurized air is applied to the sensor/sampler directed at. an angle to a measuring surfade of the sensor, the angle being between 0 and 90 degrees.

5. A method according to claim 1, wherein the sensor/sampler is arranged in working height, easy to reach for attendance, visual control and possible sensor unit replacement.

6. A method according to claim 1, wherein a level monitor is used for stopping the vacuum or pressure generating pump when the fluid with the solid substance has reached a desired level.

7. A method according to claim 6, wherein by severe fouling of the sensor, an alarm signal is generated in a fouling alarm, which is based on optical technique, by means of signals from the level monitor and the sensor.

8. A method according to claim 7, wherein manual cleaning of the measuring surface is performed with a brush when an alarm signal is received from the fouling alarm (4).

9. A method according to claim 7, wherein a cleaning agent is added to the water and pressurized air for the flushing when an alarm signal is received from the fouling alarm.

10. A method according to claim 7, wherein a mechanical cleaning of the measuring surface is initiated when an alarm signal is received from the fouling alarm, said cleaning being carried out by means of a power-driven brush or a brush driven by pressurized air/water.

11. A method according to claim 1, wherein said jet stream comprising of a combination of water and pressurized air is applied to the sensor/sampler directed at an angle to a measuring surface of the sensor, the angle being between 10 and 80 degrees.

12. A system for ensuring reliable measurement values when measuring the content of solid substance in a fluid by means of an optical sensor/sampler, said system comprising
 a) a sludge container or sludge line,
 b) a sensor/sampler arranged above the sludge container or sludge line and connected to the container or line through a hose or pipe line,
 c) a vacuum pump or alternatively a pressure generating pump for feeding the fluid with the solid substance to the sensor and being connected to a computer based control box for controlling the feeding in a measuring sequence, and
 d) water and pressurized air lines joined upstream of the optical sensor for applying a combination of water and pressurized air in the form of a jet stream to the sensor for flushing and thereby periodical cleaning the sensor.

13. A system according to claim 12, comprising a computer based control box by means of which the frequency of flushing, as well as sampling and measuring, is selected and controlled.

14. A system according to claim 12, wherein the jet of water and pressurized air is directed at an angle to a measuring surface of the sensor (1), the angle being between 0 and 90 degrees.

15. A system according to claim 12, wherein the sensor/sampler is arranged in working height, easy to reach for attendance, visual control and sensor unit replacement.

16. A system according to claim 12, comprising a level monitor adapted to stop said vacuum or pressure generating pump when the fluid containing the solid substance has reached a desired level.

17. A system according to claim 12, comprising a fouling alarm (4) that is based on optical technique and that is adapted to emit an alarm signal when receiving signals from the level monitor (5) and the sensor (1) by severe fouling of the sensor.

18. A system according to claim 17, wherein a line is connected to the water supply line for supplying cleaning agent when a corresponding alarm signal is received from the fouling alarm.

19. A system according to claim 17, further comprising one of a power-driven brush and a brush driven by pressurized air/water, said brush being adapted to be started in order to perform a mechanical cleaning of the measuring surface of the sensor when a corresponding alarm signal is received from the fouling alarm.

* * * * *